(12) United States Patent
Cheon et al.

(10) Patent No.: US 12,408,819 B2
(45) Date of Patent: Sep. 9, 2025

(54) BASKET DEVICE FOR ENDOSCOPE

(71) Applicant: ROEN Surgical, Inc., Daejeon (KR)

(72) Inventors: Byung Sik Cheon, Daejeon (KR); Dong Soo Kwon, Daejeon (KR)

(73) Assignee: ROEN Surgical, Inc., Daejeon (KR)

( * ) Notice: Subject to any disclaimer, the term of this patent is extended or adjusted under 35 U.S.C. 154(b) by 607 days.

(21) Appl. No.: 17/423,466

(22) PCT Filed: Aug. 29, 2019

(86) PCT No.: PCT/KR2019/011047
§ 371 (c)(1),
(2) Date: Jul. 15, 2021

(87) PCT Pub. No.: WO2020/149484
PCT Pub. Date: Jul. 23, 2020

(65) Prior Publication Data
US 2022/0117467 A1    Apr. 21, 2022

(30) Foreign Application Priority Data
Jan. 17, 2019   (KR) .................. 10-2019-0006321

(51) Int. Cl.
*A61B 1/00* (2006.01)
*A61B 1/012* (2006.01)
*A61B 1/018* (2006.01)

(52) U.S. Cl.
CPC ........ *A61B 1/00085* (2013.01); *A61B 1/0125* (2013.01); *A61B 1/018* (2013.01)

(58) Field of Classification Search
CPC ... A61B 1/00085; A61B 1/0125; A61B 1/018; A61B 17/221; A61B 1/00105; A61B 2017/2215; A61B 1/00137; A61B 1/00087; A61B 2017/00296; A61B 5/6858; A61B 1/0008; A61B 17/29; A61B 2017/301; A61B 2017/303; A61B 17/083; A61B 17/12013; A61B 17/1285
(Continued)

(56) References Cited

U.S. PATENT DOCUMENTS 6,110,127 A * 8/2000 Suzuki .................. A61B 10/06
606/205
2004/0034334 A1 2/2004 Ruddell et al.
(Continued)

FOREIGN PATENT DOCUMENTS

CA        2710103 A1 * 2/2011 ......... A61B 1/00149
JP        2005224262       8/2005
(Continued)

*Primary Examiner* — Michael J Carey
*Assistant Examiner* — Timothy Tuan Luu
(74) *Attorney, Agent, or Firm* — JCIPRNET

(57) ABSTRACT

A basket device for an endoscope includes a base tube attached to an end of an endoscope tube and including at least one channel through which an endoscopic camera or a surgical instrument passes, a plurality of baskets provided at locations separate from each other in a radial direction along an edge of an end of the base tube and formed to protrude in a direction in which each of the baskets is to be expanded, and an operator formed to surround the plurality of baskets at the end of the base tube and being slidable in a longitudinal direction of the base tube.

5 Claims, 3 Drawing Sheets

(58) Field of Classification Search
USPC .................................................. 606/140, 142
See application file for complete search history.

(56) References Cited

U.S. PATENT DOCUMENTS

| | | | | |
|---|---|---|---|---|
| 2005/0075665 | A1* | 4/2005 | Brenzel | A61B 17/0057 |
| | | | | 606/213 |
| 2012/0179172 | A1* | 7/2012 | Paul, Jr. | A61B 17/0057 |
| | | | | 606/151 |
| 2016/0095612 | A1* | 4/2016 | DeVille | A61B 17/32002 |
| | | | | 606/115 |
| 2017/0156745 | A1 | 6/2017 | Okada | |
| 2017/0164971 | A1* | 6/2017 | Moretti | A61B 17/221 |
| 2018/0193050 | A1* | 7/2018 | Hawkins | A61B 17/0644 |

FOREIGN PATENT DOCUMENTS

| | | | | |
|---|---|---|---|---|
| JP | 2005224262 A * | 8/2005 | ......... | A61B 1/00087 |
| KR | 101817007 | 1/2018 | | |
| WO | WO-2004064609 A2 * | 8/2004 | ....... | A61B 17/12013 |
| WO | WO-2018168832 A1 * | 9/2018 | ............. | A61B 17/22 |
| WO | 2018189774 | 10/2018 | | |
| WO | WO-2018208771 A1 * | 11/2018 | ......... | A61B 1/00085 |

* cited by examiner

[Fig. 1]
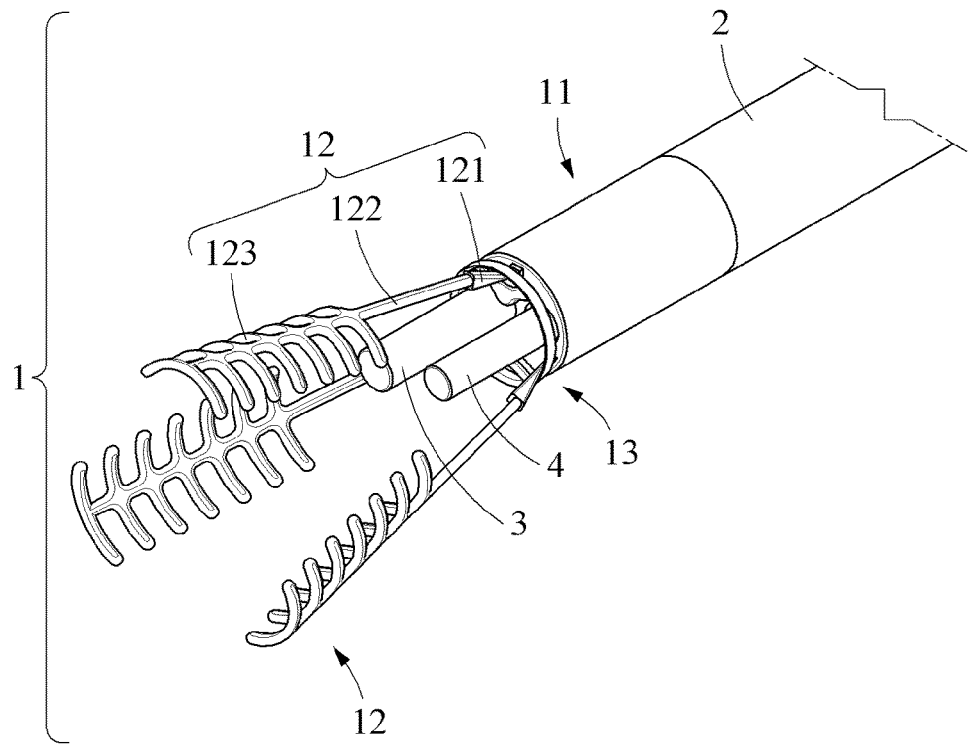
[Fig. 2a]
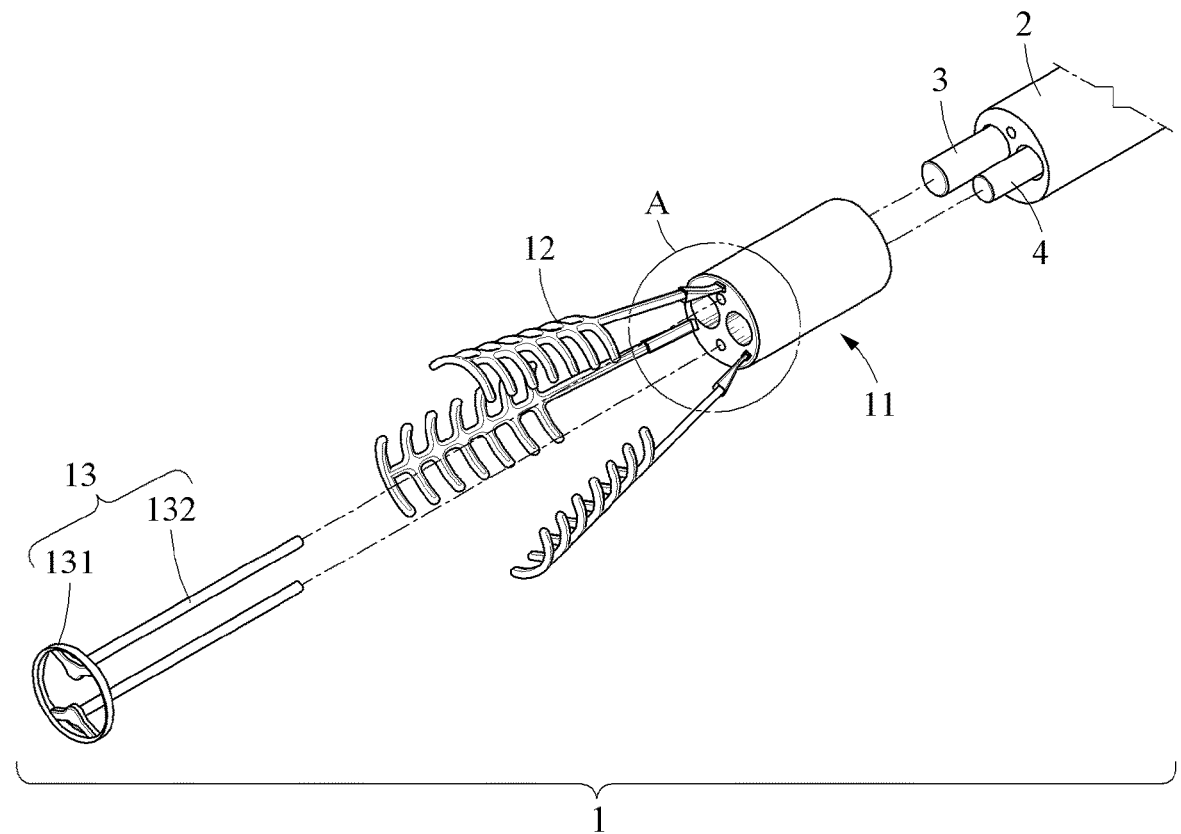

[Fig. 2b]
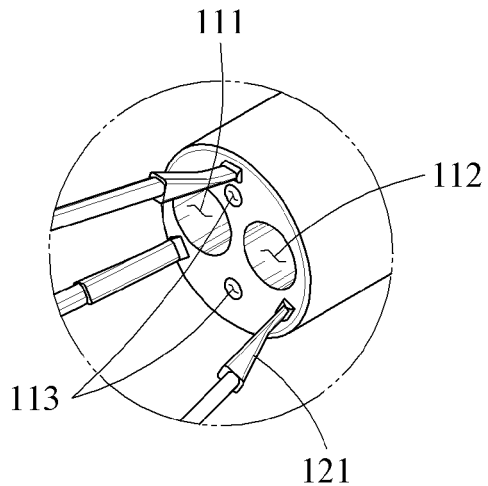
[Fig. 3]
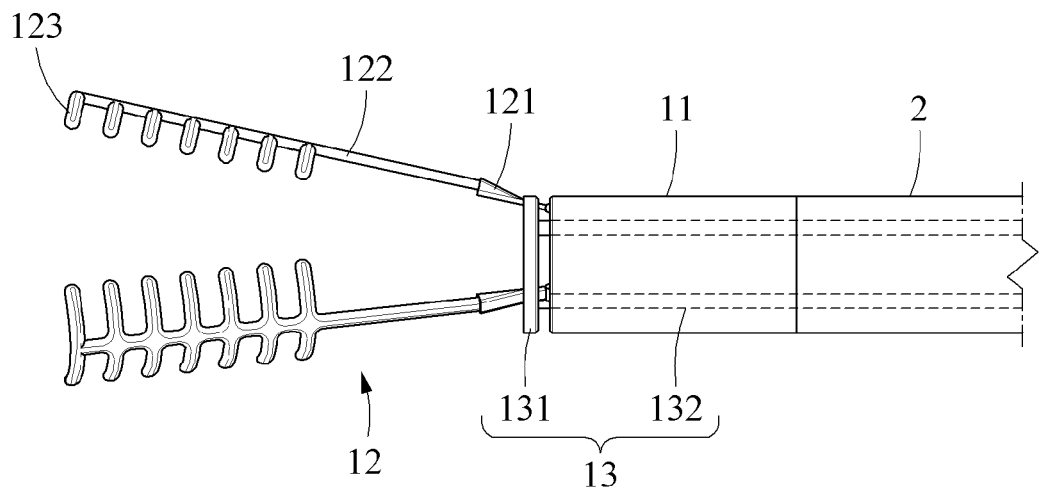
[Fig. 4]
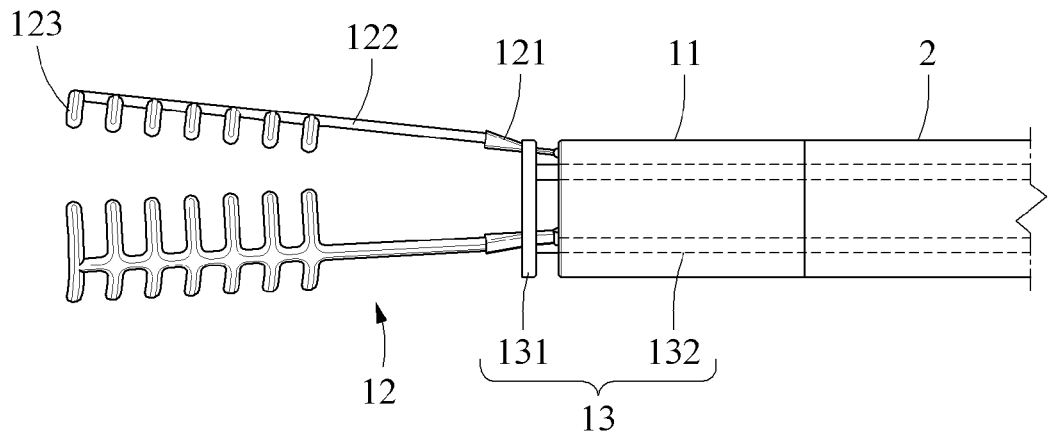

[Fig. 5]
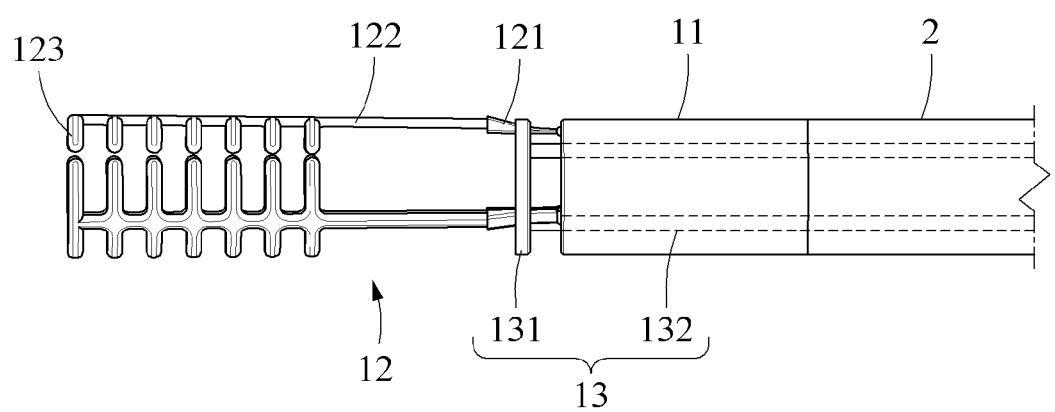

BASKET DEVICE FOR ENDOSCOPE

TECHNICAL FIELD

Example embodiments relate to a basket device for an endoscope.

BACKGROUND ART

An endoscopy may be performed to remove a foreign object such as, for example, a stone formed in a bile duct or a ureter. For the endoscopy, there is a generally used method of intubating an insertion tube of an endoscope inside a bile duct or a ureter, inserting a laser cautery into a channel of the insertion tube and destroying a stone therein, and then inserting a stone removing device to remove and capture, from an end of a tube of the endoscope, fragments of the stone generated by the destroying.

A general type of the stone removing device includes a basket of a network structure formed of a steel wire formed of a metal and having a plurality of metal wire strands gathered at a front end thereof. When the plurality of wires is inside a tube, they are contracted in a space inside the tube. However, when the plurality of wires to be pulled out of the tube is expanded in all directions, a capturing space may be formed therein to remove a stone.

However, to remove a stone through the endoscopy or an endoscopic procedure, a camera configured to capture an image, a laser configured to destroy the stone, and a basket configured to remove or capture the stone may need to be provided at a distal end of the insertion tube and used. Thus, it may be desirable to perform the endoscopic procedure by inserting all the three elements described above into a channel of the insertion tube. However, due to a spatial limitation of a narrow bile duct or ureter, it is general to provide a single available channel excluding a channel through which the camera passes.

Thus, in a case of an endoscope not having two or more available channels excluding the channel in which such endoscopic camera is installed, there is inconvenience because the stone needs to be pulverized through a laser cautery in a process of removing the stone, and the laser cautery needs to be removed from a channel to remove the pulverized ones by the basket and then the basket needs to be inserted into the channel. Thus, a great amount of time may need to be consumed, and the time consumption may be a negative factor in the endoscopic procedure that requires an extremely elaborate and precise manipulation or operation.

Thus, there is an increasing desire for the development of an endoscope device capable of performing appropriate treatment as needed, without a need to replace a basket and other surgical instruments when performing a stone removal procedure or a lithotomy through an endoscope without an additional available channel into which the basket is to be inserted.

DISCLOSURE OF INVENTION

Technical Problem

An aspect provides a basket device for an endoscope.

Solution to Problem

According to an example embodiment, there is provided a basket device for an endoscope, the basket device including a base tube attached to an end of an endoscope tube and including at least one channel through which an endoscopic camera or a surgical instrument passes, a plurality of baskets provided at locations separate from each other in a radial direction along an edge of an end of the base tube and protruding in a direction in which each of the baskets is to be expanded, and an operator formed to surround the plurality of baskets at the end of the base tube and being slidable in a longitudinal direction of the base tube.

The base tube may be detachably attachable to the end of the endoscope tube.

Each of the baskets may include a fixer provided in an edge portion of a surface of the end of the base tube, a protrusion extended in a direction to be expanded from the fixer based on the longitudinal direction of the base tube, and a gripper connected to the protrusion, and configured to be assembled towards a central axis of the base tube based on an operation of the operator and grab a foreign object.

The gripper may be formed to protrude in both directions from a plurality of locations separate from each other along a protruding direction of the protrusion, and having a rake shape protruding to be curved towards an axis of the longitudinal direction of the base tube.

The base tube may further include a sliding hole not communicating with the channel and formed to be recessed from the end of the base tube. The operator may include an annular member provided in an edge portion of the end of the base tube and configured to surround the plurality of baskets, and an inserter connected to the annular member to be slidably inserted into the sliding hole.

The sliding hole may be provided as a plurality of sliding holes at points separate from each other at regular intervals in a radial direction from the end of the base tube. The inserter may be provided as a plurality of inserters at points separate from each other at regular intervals in a radial direction from the annular member such that the inserters are to be inserted into the sliding holes, respectively.

In the fixer, a portion to be in contact with an inner circumferential surface of a cavity of the annular member may have a shape inclined outwards from the central axis of the base tube towards the protrusion.

Advantageous Effects of Invention

According to example embodiments described herein, there is provided a basket device for an endoscope. A basket may not be inserted in a channel of an insertion tube, and thus the number of available channels may increase and the degree of freedom for an operation or a surgery may also increase.

According to example embodiments described herein, there is provided a basket device for an endoscope that may be compatible with a generally used endoscope device because it is detachably attachable to an end tip of an insertion tube.

According to example embodiments described herein, there is provided a basket device for an endoscope that may not have a protrusion protruding from an outer portion of a circumference of an insertion tube when a basket is contracted maximally, and thus may not have an unnecessarily interfering portion during an endoscopic procedure.

BRIEF DESCRIPTION OF DRAWINGS

FIG. 1 is a perspective view of a basket device for an endoscope according to an example embodiment.

FIGS. 2a and 2b are an exploded perspective view of a basket device for an endoscope, and an enlarged view of a portion thereof according to an example embodiment.

FIG. 3 is a side view of a basket device for an endoscope in which a basket is expanded according to an example embodiment.

FIG. 4 is a side view of a basket device for an endoscope in which a basket is partially contracted according to an example embodiment.

FIG. 5 is a side view of a basket device for an endoscope in which a basket is fully contracted according to an example embodiment.

MODE FOR THE INVENTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Terms such as first, second, A, B, (a), (b), and the like may be used herein to describe components. Each of these terminologies is not used to define an essence, order, or sequence of a corresponding component but used merely to distinguish the corresponding component from other component(s). For example, a first component may be referred to as a second component, and similarly the second component may also be referred to as the first component. In addition, it should be noted that if it is described in the specification that one component is "connected," "coupled," or "joined" to another component, a third component may be "connected," "coupled," and "joined" between the first and second components, although the first component may be directly connected, coupled or joined to the second component.

Components included in one embodiment may have the same name as a component having the same function in other embodiments. Unless otherwise stated, a description of the one embodiment may be applied to the other embodiments. A detailed description of overlapping portions between embodiments will be omitted.

FIG. 1 is a perspective view of a basket device for an endoscope according to an example embodiment. FIGS. 2a and 2b are an exploded perspective view of a basket device for an endoscope, and an enlarged view of a portion thereof according to an example embodiment. FIG. 3 is a side view of a basket device for an endoscope in which a basket is expanded according to an example embodiment. FIG. 4 is a side view of a basket device for an endoscope in which a basket is partially contracted according to an example embodiment. FIG. 5 is a side view of a basket device for an endoscope in which a basket is fully contracted according to an example embodiment.

Referring to FIGS. 1 through 5, a basket device 1 for an endoscope is attached to an end tip of an insertion tube 2 of a commercially used endoscope. For example, the basket device 1 is inserted into a bile duct or a ureter while being attached to an end of the insertion tube 2 of the endoscope, or inserted into an interior of a guide sheath that is inserted in advance in a bile duct or a ureter.

For example, the insertion tube 2 includes a plurality of channels formed therein along a longitudinal direction thereof. A surgical instrument such as an endoscopic camera 3 or a laser cautery 4 is inserted in the channels, and the surgical instrument inserted in the channels protrudes from the end tip of the insertion tube 2.

For example, as illustrated, the basket device 1 includes a base tube 11, an operator 13, and a plurality of baskets 12.

The base tube 11 is attached to the end of the insertion tube 2 of the endoscope. For example, the base tube 11 is provided in a cylindrical shape having a same diameter as that of the insertion tube 2. For example, the base tube 11 is formed of a flexible plastic material.

For example, when the base tube 11 is provided in the insertion tube 2, one or more channels 111 and 112 of the base tube 11 and the channels of the insertion tube 2 may be overlapped to communicate with one another.

The base tube 11 includes the one or more channels 111 and 112, and a sliding hole 113. The one or more channels 111 and 112 include a camera channel 111 and a surgical instrument channel 112.

The camera channel 111 may be a hole formed in a longitudinal direction of the base tube 11 to communicate with a channel through which the endoscopic camera 3 passes among the channels of the insertion tube 2.

The surgical instrument channel 112 may be a hole formed in the longitudinal direction of the base tube 11 to communicate with a channel through which a surgical instrument such as the laser cautery 4 passes among the channels of the insertion tube 2.

Alternatively, the camera channel 111 and the surgical instrument channel 112 may be construed as being a partial region of a single cavity formed along a central axis of the base tube 11. That is, the one or more channels 111 and 112 may be formed as a single cavity.

The sliding hole 113 may be a hole formed in the longitudinal direction of the base tube 11 to allow an inserter 132 of the operator 13 to be slidably inserted therein.

For example, the sliding hole 113 is recessed at points separate from each other at regular intervals in a radial direction on a surface of an end of the base tube 11. Thus, through this, such sliding operation of the operator 13 may be accurately guided in the longitudinal direction of the base tube 11 to be accurately performed. The operator 13 is disposed at the end of the base tube 11 and formed to surround the baskets 12, and configured to slide with respect to the base tube 11 to allow the baskets 12 to be contracted or expanded.

For example, the operator 13 includes an annular member 131 provided in an edge portion of the end of the base tube 11 and formed to surround the baskets 12, and the inserter 132 connected to the annular member 131 and configured to be slidably inserted into the sliding hole 113.

The annular member 131 has a diameter less than or equal to that of the base tube 11, and a cavity formed therein is configured to accommodate the baskets 12.

The inserter 132 is a rod-shaped member extending from an edge portion of the annular member 131 in the longitudinal direction of the base tube 11 to be inserted into the sliding hole 113 of the base tube 11. For example, the inserter 132 extends from the edge portion of the annular member 131 in the longitudinal direction of the base tube 11 to be inserted into the sliding hole 113 of the base tube 11.

For example, the inserter 132 is formed at each of points separate from each other at regular intervals in a radial direction from the edge portion of the annular member 131. In this example, a plurality of inserters 132 is configured to be inserted into a plurality of sliding holes 113 formed at points separate from each other at regular intervals in a radial direction from the surface of the end of the base tube 11.

Through such structure, the annular member 131 slides in the longitudinal direction of the base tube 11 when the operator 13 slides along the longitudinal direction of the base tube 11. Based on a location of the annular member 131, an assembly angle of each of the baskets 12 may change, and thus contraction or expansion may be performed through the baskets 12.

For example, the inserter 132 passes through the base tube 11 to be connected to the insertion tube 2. In this example, the insertion tube 2 may include an additional medium configured to be connected to the inserter 132 to slide the inserter 132 forwards and backwards from the base tube 11.

The baskets 12 are provided at locations separate from each other at regular intervals in a radial direction from the surface of the end of the base tube 11, each formed to protrude in a direction expanding or spreading from the longitudinal direction of the base tube 11 or formed to protrude in a direction receding from an axis of the longitudinal direction to protrude in the longitudinal direction of the base tube 11.

For example, as illustrated in FIGS. 1, and 2a and 2b, the baskets 12 are provided at the locations separate from each other in a radial direction in an edge portion of the surface of the end of the base tube 11, and formed to protrude to expand or spread outwards after passing through the cavity of the annular member 131.

For example, the baskets 12 are formed with a flexible metal or a plastic material. Thus, after the baskets 12 are contracted by the sliding operation of the operator 13 as illustrated in FIG. 5, and then the operator 13 is pulled back as illustrated in FIG. 3, the baskets 12 return to have their original expanding angles.

Each of the baskets 12 includes a fixer 121 provided in the edge portion of the surface of the end of the base tube 11, a protrusion 122 extending in a direction expanding from the fixer 121 from the longitudinal direction of the base tube 11, and a gripper 123 formed to protrude in both directions of the protrusion 122.

The fixer 121 may be a portion fixed to the surface of the end of the base tube 11. For example, the fixer 121 of each of the baskets 12 is in contact with an inner circumferential surface of the cavity of the annular member 131 while being accommodated in the annular member 131.

For example, the fixer 121 is formed in a shape that expands outwards as it recedes from the base tube 11 in the longitudinal direction of the base tube 11. That is, a portion of the fixer 121 that is in contact with the inner circumferential surface of the cavity of the annular member 131 is formed in a shape inclined in an outward direction from the central axis of the base tube 11 towards the protrusion 122. For example, an angle between the central axis of the base tube 11 and the fixer 121 may be greater than an angle between the central axis of the base tube 11 and the protrusion 122. Through such structure, an assembly angle of the protrusion 122 may increase when the operator 13 slides, and thus a rapid operation may be performed.

When the baskets 12 are assembled towards an inner side of the base tube 11 through a forward sliding operation or motion of the operator 13 and contracted thereby, the gripper 123 grabs a foreign object such as a stone.

For example, the gripper 123 is formed to protrude in both sides from each of points in a portion of the protrusion 122. The gripper 123 protrudes in both directions from the protrusion 122, and is formed to be curved towards the axis of the longitudinal direction of the base tube 11 or curved inwards in a radial direction of the base tube 11. That is, the gripper 123 of the baskets 12 is formed in a rake shape. For example, when the baskets 12 are contracted to be closer to one another as illustrated in FIG. 5, a shape of an arc formed as the gripper 123 of each of the baskets 12 is curved forms an edge of a single circle. However, the shape of the gripper 123 is not limited to what is illustrated in the accompanying drawings.

Hereinafter, how the baskets 12 are assembled together by the sliding operation or motion of the operator 13 will be described in detail with reference to FIGS. 3 through 5.

For example, as illustrated in FIG. 3, when the annular member 131 is located close to the base tube 11, the baskets 12 may be in a state expanding or spreading outwards along the longitudinal direction of the base tube 11, and approach a foreign object to be removed or captured while being in this state such that the foreign object is to be located between the baskets 12 and the gripper 123.

Subsequently, as illustrated in FIG. 4, when the operator 13 slides in a forward direction of the base tube 11, the baskets 12 are pressed by the annular member 131 moving forwards and then assembled together in an inward direction, and thus the gripper 123 of each of the baskets 12 becomes closer to one another to grab a foreign object.

In addition, to finish grabbing a foreign object or to grab a smaller foreign object, the operator 13 may further slide in a forward direction. In such case, the baskets 12 may be contracted until they are disposed to be in parallel with one another. For example, while being fully contracted, the baskets 12 may not protrude out of a radius range formed by an outer circumferential surface of the base tube 11 with respect to the axis of the longitudinal direction of the base tube 11. Through such structure, when the insertion tube 2 including the basket device 1 is inserted directly into a bile duct or a ureter, or into a guide sheath that is inserted in advance in a bile duct or a ureter, and then moves, it is possible to prevent the baskets 12 from excessively interfering in an external tissue or the guide sheath and from hindering the insertion tube 2 from being inserted and moving.

According to an example embodiment described herein, the baskets 12 are not inserted into a channel of the insertion tube 2, and it is thus possible to increase the number of available channels and increase the degree of freedom of a surgery or a surgical procedure. In addition, the basket device 1 is detachably attachable to an end tip of the insertion tube 2 and is thus compatibly applied to a commercially used endoscope.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A basket device for an endoscope, comprising:
a base tube attached to an end of an endoscope tube, and including at least one channel through which an endoscopic camera or a surgical instrument passes;
a plurality of baskets provided at locations separate from each other in a radial direction along an edge of an end of the base tube, and protruding in a direction in which each of the baskets is to be expanded; and
an operator formed to surround the plurality of baskets at the end of the base tube and being slidable in a longitudinal direction of the base tube, wherein
the base tube further comprises:
a sliding hole not communicating with the channel and formed to be recessed from the end of the base tube,
the operator comprises:
an annular member provided in an edge portion of the end of the base tube and configured to surround the plurality of baskets; and
an inserter connected to the annular member to be slidably inserted in the longitudinal direction of the base tube into the sliding hole, and configured to slide forwards and backwards from the base tube, and
each of the baskets comprises a fixer fixed to an edge portion of a surface of the end of the base tube;
wherein the sliding hole is provided as a plurality of sliding holes at points separate from each other at regular intervals in a radial direction from the end of the base tube, and
the inserter is provided as a plurality of inserters at points separate from each other at regular intervals in a radial direction from the annular member such that the inserters are to be inserted into the sliding holes, respectively.

2. The basket device of claim 1, wherein the base tube is detachably attachable to the end of the endoscope tube.

3. The basket device of claim 1, wherein each of the baskets further comprises:
a protrusion extended in a direction to be expanded from the fixer based on the longitudinal direction of the base tube; and
a gripper connected to the protrusion, and configured to be assembled towards a central axis of the base tube based on an operation of the operator and grab a foreign object.

4. The basket device of claim 3, wherein the gripper is formed to protrude in both directions along a circumferential axis from a plurality of locations separate from each other along a protruding direction of the protrusion, and having a rake shape protruding to be curved towards an axis of the longitudinal direction of the base tube.

5. The basket device of claim 3, wherein, in the fixer, a portion to be in contact with an inner circumferential surface of a cavity of the annular member has a shape inclined outwards from the central axis of the base tube towards the protrusion.

* * * * *